United States Patent
Pappas et al.

(10) Patent No.: US 8,663,610 B2
(45) Date of Patent: Mar. 4, 2014

(54) METHOD OF MAKING AN ANHYDROUS LIQUID ANTIPERSPIRANT COMPOSITION

(75) Inventors: Iraklis Pappas, Pennsauken, NJ (US); Michael C. Fitzgerald, Oakhurst, NJ (US); Long Pan, Cherry Hill, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/518,944

(22) PCT Filed: Dec. 16, 2010

(86) PCT No.: PCT/US2010/060630
§ 371 (c)(1), (2), (4) Date: Jun. 25, 2012

(87) PCT Pub. No.: WO2011/087701
PCT Pub. Date: Jul. 21, 2011

(65) Prior Publication Data
US 2012/0282206 A1    Nov. 8, 2012

Related U.S. Application Data

(60) Provisional application No. 61/289,433, filed on Dec. 23, 2009.

(51) Int. Cl.
*A61K 8/26*   (2006.01)

(52) U.S. Cl.
USPC .............................................. 424/65; 424/68

(58) Field of Classification Search
None
See application file for complete search history.

(56) References Cited

U.S. PATENT DOCUMENTS

| | | | |
|---|---|---|---|
| 2,230,082 | A | 1/1941 | Montenier |
| 2,236,387 | A | 3/1941 | Wallace et al. |
| 3,928,557 | A | 12/1975 | Wright et al. |
| 3,932,609 | A | 1/1976 | Rosenstreich et al. |
| 3,981,986 | A | 9/1976 | Rubino |
| 4,069,299 | A | 1/1978 | Hodgson |

(Continued)

FOREIGN PATENT DOCUMENTS

| CA | 2257559 | 12/1997 |
|---|---|---|
| DE | 102005026355 | 12/2006 |

(Continued)

OTHER PUBLICATIONS

Morrison et al. "Characterization of thermal behavior of deep eutectic solvents and their potential as drug solubilization vehicles," International Journal of Pharmaceutics 387:136-139, available online May 27, 2009.*

(Continued)

*Primary Examiner* — Kortney L Klinkel
*Assistant Examiner* — Alissa Prosser
(74) *Attorney, Agent, or Firm* — Michael F. Morgan

(57) ABSTRACT

A method of producing an anhydrous antiperspirant composition comprising (a) providing a mixture of at least one antiperspirant active including a metal salt, and an anhydrous carrier for the at least one antiperspirant active in which the at least one antiperspirant active is dissolved, the carrier comprising a eutectic mixture of at least one basic compound selected from a basic amide and a basic amine and at least one member chosen from a cation and zwitterion; and (b) heating the mixture to form a stabilized eutectic system of the at least one antiperspirant active and the anhydrous carrier. Also, an anhydrous antiperspirant composition.

16 Claims, 2 Drawing Sheets

(56) References Cited

U.S. PATENT DOCUMENTS

| | | | |
|---|---|---|---|
| 4,113,852 | A | 9/1978 | Kenkare et al. |
| 4,137,306 | A * | 1/1979 | Rubino et al. ............... 424/68 |
| 4,777,034 | A | 10/1988 | Olivier et al. |
| 5,676,936 | A | 10/1997 | Park |
| 6,007,799 | A | 12/1999 | Lee et al. |
| 6,375,937 | B1 | 4/2002 | Chopra et al. |
| 6,960,338 | B2 | 11/2005 | Li et al. |
| 7,074,394 | B2 | 7/2006 | Li et al. |
| 7,105,691 | B2 | 9/2006 | Holerca et al. |
| 7,303,743 | B2 | 12/2007 | Hurley et al. |
| 2003/0044368 | A1 | 3/2003 | Tsuchikura |
| 2004/0077519 | A1 | 4/2004 | Price et al. |
| 2004/0097755 | A1 | 5/2004 | Abbott et al. |
| 2004/0109833 | A1 | 6/2004 | Tang et al. |
| 2004/0198998 | A1 | 10/2004 | Holerca et al. |
| 2006/0094620 | A1 | 5/2006 | Jordan et al. |
| 2006/0094621 | A1 | 5/2006 | Jordan et al. |
| 2006/0099163 | A1 * | 5/2006 | Hurley et al. ............... 424/68 |
| 2006/0204463 | A1 | 9/2006 | Tang et al. |
| 2007/0110687 | A1 | 5/2007 | Mattai et al. |
| 2007/0196303 | A1 * | 8/2007 | Li et al. ............ 424/68 |
| 2007/0196308 | A1 | 8/2007 | Popoff et al. |
| 2008/0070966 | A1 | 3/2008 | Elder et al. |
| 2009/0257970 | A1 | 10/2009 | Bloom |

FOREIGN PATENT DOCUMENTS

| | | |
|---|---|---|
| EP | 0281812 | 9/1988 |
| EP | 0914138 | 5/1999 |
| WO | WO 2006/091417 | 8/2006 |
| WO | WO 2007/059530 | 5/2007 |
| WO | WO 2007/064756 | 6/2007 |
| WO | WO 2008/155464 | * 12/2008 |
| WO | WO 2011/079001 | 6/2011 |
| WO | WO 2011/087702 | 7/2011 |

OTHER PUBLICATIONS

The website Chemical Book entry for urea, 2008 http://www.chemicalbook.com/ProductChemicalPropertiesCB5853861_EN.htm.*

The website Chemical Book entry for trimethylglycine, 2008 http://www.chemicalbook.com/ProductChemicalPropertiesCB0760102_EN.htm.*

Abbott et al., 2003, "Novel Solvent Properties of Choline Chloride/Urea Mixtures", Chemical Communications 2003(1):70-71.

Abbott et al., 2004, "Deep Eutectic Solvents Formed between Choline Chloride and Carboxylic Acids: Versatile Alternatives to Ionic Liquids", Journal of The American Chemical Society 126:9142-9147.

Binnemans, 2005, "Ionic Liquid Crystals", Chemical Reviews 105:4148-4204.

Binnesmans, 2007, "Lanthanides and Actinides in Ionic Liquids", Chemical Reviews 107:2592-2614.

Chi et al., 1998, "Preventing Discoloration of Squalene-soiled Cotton Fabrics with Antioxidants", Journal of Surfactants and Detergents 1(4):523-527.

Coehlo-Sampaio et al., 1994, "Betaine Counteracts Urea-induced Conformational Changes and Uncoupling of the Human Erythrocyte $Ca^{2+}$ Pump", European Journal of Biochemistry 221:1103-1110.

Davis et al., 2003, "From Curiosities to Commodities: Ionic Liquids Begin the Transition", Chemical Communications 11:1209-1212.

Dupont et al., 2002, "Ionic Liquid (Molten Salt) Phase Organometallic Catalysis", Chemical Reviews 102:3667-3692.

Endres et al., 2006, "Air and Water Stable Ionic Liquids in Physical Chemistry", Physical Chemistry Chemical Physics 8:2101-2116.

FDA, 1978, Monograph on Antiperspirant Dry Products, Oct. 10, 1978.

Feng et al., 2007, "Speciation of Hydroxyl-Al Polymers Formed through Simultaneous Hydrolysis of Aluminum Salts and Urea", Colloids & Surfaces A 303:241-248.

Greaves et al., 2008, "Protic Ionic Liquids: Properties and Applications", Chemical Reviews 108:206-237.

Hardacre et al., 2007, "Structure and Solvation in Ionic Liquids", Accounts of Chemical Research 40:1146-1155.

Holzle et al., 1984, "Structural Changes in Axillary Eccrine Glands Following Long-term Treatment with Aluminium Chloride Hexahydrate Solution", British Journal of Dermatology 110:399-403.

Hu et al., 2005, "Effects of the Structures of Ionic Liquids on Their Physical-Chemical Properties and the Phase Behavior of Mixtures Involving Ionic Liquids", Section 7.1 "Effect of Cation Structures".

Huddleston et al., 2001, "Characterization and Comparison of Hydrophilic and Hydrophobic Room Temperature Ionic Liquids Incorporating the Imidazolium Cation", Green Chemistry 3:156-164.

Morrison, et al., 2009, Characterization of Thermal Behavior of Deep Eutectic Solvents and Their Potential as Drug Solubilization Vehicles, International Journal of Pharmacy 378:136-139.

Nockemann et al., 2006, "Task-Specific Ionic Liquid for Solubilizing Metal Oxides", Journal of Physical Chemistry B 110:20978-20992.

Padua et al., 2007, "Molecular Solutes in Ionic Liquids: A Structural Perspective", Accounts of Chemical Research 40:1087-1096.

Parnham et al., 2007, "Ionothermal Synthesis of Zeolites. Metal-Organic Frameworks, and Inorganic-Organic Hybrids", Accounts of Chemical Research 40:1005-1013.

Parvulesen et al., 2007, "Catalysis in Ionic Liquids", Chemical Reviews 107:2615-2665.

PCT/US2010/060630—ISR and Written Opinion mailed May 25, 2012.

PCT/US2010/060633—ISR and Written Opinion mailed May 24, 2012.

PCT/US2010/060634—ISR and Written Opinion mailed May 25, 2012.

Plechkova et al., 2008, "Applications of Ionic Liquids in the Chemical Industry", Chemical Society Reviews 37:123-150.

Ranke et al., 2007, "Design of Sustainable Chemical Products—The Example of Ionic Liquids", Chemical Reviews 107:2183-2206.

Rantwijk et al., 2007, "Biocatalysts in Ionic Liquids", Chemical Reviews 107:2757-2785.

Rogers et al., 2007, "Ionic Liquids", Accounts of Chemical Research 40(11):1077-1078.

RSC, 2005, "Salty Solvents—Ionic Really", Royal Society of Chemicals.

Schaber et al., 2004, "Thermal Decomposition (pyrolysis) of Urea in an Open Reaction Vessel", Thermochimicta Acta 424:131-142.

Shafran et al., 2004, "High Temperature Speciation Studies of Al-Ion Hydrolysis", Advanced Engineering Materials 6(10):836-839.

Shaw et al., 1955, "The Decomposition of Urea in Aqueous Media", Journal of the American Chemistry Society 77(18):4729-4733.

Short, 2006. "Out of the Ivory Tower: Ionic Liquids Are Starting to Leave Academic Labs and Find Their Way into a Wide Variety of Industrial Applications", Chemical & Engineering News 84(17):15-21.

Smiglak et al., 2007, "The Second Evolution of Ionic Liquids: From Solvents and Separations to Advanced Materials—Energetic Examples from the Ionic Liquid Cookbook", Accounts of Chemical Research 40: 1182-1192.

Vogels et al., 2005, "Homogeneous Forced Hydrolysis of Aluminum Through the Thermal Decomposition of Urea", Journal of Colloid and Interface Science 285:86-93.

Wang et al., 2006, "A Theoretical Investigation of the Interactions between Water Molecules and Ionic Liquids", Journal of Physical Chemistry B 110:24646-24651.

Welton, 1999, "Room-Temperature Ionic Liquids, Solvents for Synthesis and Catalysis", Chemical Reviews 99:2071-2083.

Wikipedia entry, 2004, "Ionic Liquid".

Wikipedia entry, 2005, "Deep Eutectic Solvent".

Yancey et al., 1982, "Living with Water Stress: Evolution of Osmolyte Systems", Science 217: 1214-1222.

* cited by examiner

METHOD OF MAKING AN ANHYDROUS LIQUID ANTIPERSPIRANT COMPOSITION

CROSS REFERENCE TO RELATED APPLICATIONS

This application is a national stage entry under 35 U.S.C. §371 of International Patent Application No. PCT/US2010/060630, filed 16 Dec. 2010, which claims priority to U.S. Provisional Patent Application Ser. No. 61/289,433, filed on 23 Dec. 2009, which are incorporated herein by reference.

BACKGROUND

There have been several forms of antiperspirant products, such as sticks, soft solids, roll-ons, and aerosols. The antiperspirant products may additionally contain deodorant actives. The different forms deliver antiperspirant actives, and optionally deodorant actives, to axillary areas. There can be disadvantages when formulating these types of products.

One disadvantage is that when an antiperspirant active is included, steps need to be taken to stabilize the antiperspirant from hydrolyzing and polymerizing during storage. When an antiperspirant polymerizes into larger species, the efficacy is reduced.

Another disadvantage is that materials used for delivery, such as in the sticks or soft solids, can leave a white residue on the skin. This can be aesthetically unpleasing when seen on skin or when transferred to clothing during wearing.

It would be advantageous to develop a new form of delivery of antiperspirant and/or deodorant actives.

SUMMARY

Provided is method of producing an anhydrous antiperspirant composition comprising (a) providing a mixture of at least one antiperspirant active including a metal salt, and an anhydrous carrier for the at least one antiperspirant active in which the at least one antiperspirant active is dissolved, the carrier comprising a eutectic mixture of at least one basic compound selected from a basic amide and a basic amine and at least one member chosen from a cation and zwitterion; and (b) heating the mixture to form a stabilized eutectic system of the at least one antiperspirant active and the anhydrous carrier.

Also provided is an anhydrous antiperspirant composition comprising: (a) at least one antiperspirant active including a metal salt, and (b) an anhydrous carrier for the at least one antiperspirant active in which the at least one antiperspirant active is dissolved, the carrier comprising a eutectic mixture of at least one basic compound selected from a basic amide and a basic amine and at least one member chosen from a cation and zwitterion.

DETAILED DESCRIPTION

Figure 1:
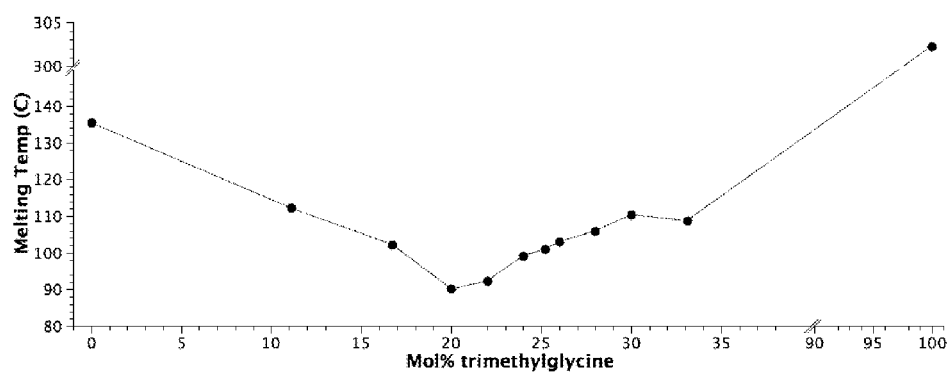
FIG. 1 is a graph showing the relationship between melting temperature and composition of a eutectic carrier for an antiperspirant active produced in accordance with one embodiment.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material unless otherwise specified.

By anhydrous it is meant that the composition contains 5 weight % or less free water. In other embodiments, the maximum amount of water is 4, 3, 2, or 1 weight %. In one embodiment, the maximum amount of water is 2 weight %. In certain embodiments, there is no free water. When calculating the water, water molecules that are part of a hydrate of a material are not counted. Too much water in the composition can hydrolyze the antiperspirant active to polymerize it, which reduces it effectiveness.

In one embodiment, the composition is a liquid at 0° C. to 100° C. In one embodiment, the composition is a liquid at 100° C. or below, or 80° C. or below. In another embodiment, the composition is a liquid at 30° C. or below.

Provided is an anhydrous antiperspirant composition comprising: (a) at least one antiperspirant active including a metal salt, and (b) an anhydrous carrier for the at least one antiperspirant active in which the at least one antiperspirant active is dissolved, the carrier comprising a eutectic mixture of at least one basic compound selected from a basic amide and a basic amine and at least one member chosen from a cation and zwitterion.

Typically, the eutectic mixture is a liquid at a temperature of up to 100° C., optionally up to 80° C., further optionally up to 30° C.

Optionally, the at least one antiperspirant active, the at least one basic compound and the at least one member chosen from a cation and zwitterion form a ternary eutectic system.

Optionally, the at least one basic compound is a hydrogen bond donor. The at least one basic compound may be selected from at least one of urea, dimethyl urea, arginine, lysine, acetamide, and guanidine.

Optionally, the at least one member chosen from a cation and zwitterion is a proton-accepting zwitterionic stabilizing ligand. The at least one proton-accepting zwitterionic stabilizing ligand may comprise at least one methylamine or may be selected from at least one of trimethylglycine, trimethylglycine hydrochloride, trimethylamine N-oxide (TMAO), carnitine, sarcosine, opine, taurine, and choline.

Betaine in IUPAC nomenclature is 1-carboxy-N,N,N-trimethylmethanaminium hydroxide-inner salt, with alternative names including carboxymethyl-trimethyl-ammonium betaine or (carboxymethyl)trimethylammonium hydroxide-inner salt or glycine betaine or glycol betaine or glycyl betaine or trimethylglycine or trimethylglycol. Betaine is not to be confused with betaine surfactants.

In one preferred embodiment, the at least one basic compound is urea and the at least one member chosen from a cation and zwitterion is trimethylglycine. Typically, the urea and trimethylglycine are in a molar ratio of 9:1 to 1.5:1, optionally 5:1 to 3:1, for example about 4:1.

Optionally, the at least one basic compound is urea and the at least one member chosen from a cation and zwitterion is trimethylglycine, and the urea and trimethylglycine form a ternary eutectic mixture with the antiperspirant active.

Optionally, the antiperspirant active is present in an amount of 5 to 25 weight %.

Typically, the antiperspirant active comprises an aluminum salt. In a preferred embodiment, the antiperspirant active comprises $AlCl_3.6H_2O$. In a particularly preferred embodiment, the ternary eutectic mixture comprises $AlCl_3.6H_2O$ as the antiperspirant active, urea and trimethylglycine. Typically, the ternary eutectic mixture comprises 5 to 25 wt % $AlCl_3 6H_2O$, 35 to 75 wt % urea, and 15 to 50 wt % trimethylglycine.

Typically, the antiperspirant composition has a pH of 2.5 to 6, optionally 3 to 5.

The anhydrous antiperspirant composition preferably comprises at most 2 wt % water.

Also provided is a method of producing an anhydrous antiperspirant composition, the method comprising the steps of: (a) providing a mixture of at least one antiperspirant active including a metal salt, and an anhydrous carrier for the at least one antiperspirant active in which the at least one antiperspirant active is dissolved, the carrier comprising a eutectic mixture of at least one basic compound selected from a basic amide and a basic amine and at least one member chosen from a cation and zwitterion; and (b) heating the mixture to form a stabilized eutectic system of the at least one antiperspirant active and the anhydrous carrier.

Preferably, the mixture comprises at most 2 wt % water.

Optionally, in step (b) the mixture is heated to melt the carrier and dissolve the at least one antiperspirant active therein. Further optionally, in step (b) the mixture is heated at a temperature below the melting temperature of each of the at least one basic compound and the at least one member chosen from a cation and zwitterion. Typically, in step (b) the mixture is heated at a temperature of at least 100° C. for a period of up to less than 3 hours, for example at a temperature of 100° C. to 150° C. for a period of 30 minutes to less than 3 hours.

Typically, the stabilized eutectic system is a liquid at a temperature of up to 100° C., optionally up to 80° C., further optionally up to 30° C.

In a particularly preferred embodiment, the at least one antiperspirant active, the at least one basic compound and at least one member chosen from a cation and zwitterion form a ternary eutectic system.

The at least one basic compound may be a hydrogen bond donor. Typically, the at least one basic compound is selected from at least one of urea, dimethyl urea, arginine, lysine, acetamide, and guanidine.

The at least one member chosen from a cation and zwitterion may be a proton-accepting zwitterionic stabilizing ligand. Typically, the at least one proton-accepting zwitterionic stabilizing ligand comprises at least one methylamine or is selected from at least one of trimethylglycine, trimethylglycine hydrochloride, trimethylamine N-oxide (TMAO), carnitine, sarcosine, opine, taurine, and choline. In a preferred embodiment, the at least one basic compound is urea and the at least one member chosen from a cation and zwitterion is trimethylglycine. Typically, the urea and trimethylglycine are in a molar ratio of 9:1 to 1.5:1, optionally 5:1 to 3:1, for example about 4:1.

In a preferred embodiment, the at least one basic compound is urea and the at least one member chosen from a cation and zwitterion is trimethylglycine, and the urea and trimethylglycine form a ternary eutectic mixture with the antiperspirant active.

Typically, the antiperspirant active is present in an amount of 5 to 25 weight %.

The antiperspirant active typically comprises an aluminum salt. In one embodiment, the antiperspirant active comprises $AlCl_3.6H_2O$. The ternary eutectic mixture may comprise $AlCl_3.6H_2O$ as the antiperspirant active, urea and trimethylglycine. Optionally, the ternary eutectic mixture comprises 5 to 25 wt % $AlCl_3.6H_2O$, 35 to 75 wt % urea, and 15 to 50 wt % trimethylglycine.

Typically, the anhydrous antiperspirant composition has a pH of 2.5 to 6, optionally 3 to 5.

The present inventors have found that a stable antiperspirant system incorporating an aluminum salt can comprise a room-temperature eutectic mixture, which is therefore liquid at room temperature, 30° C. or below, which is essentially anhydrous. The present inventors also found that by appropriately altering the reaction conditions, it is possible to affect the distribution of aluminum species as determined by size exclusion chromatography (SEC) and $^{27}Al$ NMR spectroscopy.

The melting points of pure urea and pure trimethylglycine (TMG) are 136° C. and 302° C., respectively. The melting point may be determined by Differential Scanning calorimetry (DSC). The present inventors found that urea and TMG are capable of forming a low-melting liquid, having a melting point of <120° C., when mixed within a molar ratio range of urea:TMG of 9:1 to 1.5:1, and in particular a eutectic mixture is formed which has a melting point lower than either of the constituent compounds, urea and TMG. The melting point reaches a minimum when the molar ratio of urea:TMG is 4:1.

A similar eutectic behavior is present in other systems, where urea is present as the at least one basic compound, for example when the zwitterion comprises choline, e.g. being present as choline chloride.

The present inventors also found, in a particular embodiment, that the addition to such a eutectic mixture of an antiperspirant active aluminum salt such as $AlCl_3.6H_2O$ in amounts up to 25 wt % was capable of decreasing the melting point of such a eutectic mixture to about 60-80° C. This formed a ternary eutectic mixture. In the presence of an antiperspirant active aluminum salt such as $AlCl_3.6H_2O$, the mixtures are stable below room temperature for an indefinite period of time.

The present inventors have further found that the ternary eutectic of urea, TMG, and $AlCl_3.6H_2O$ contains a significant amount of SEC Peak 4 or Peak 5 species. This indicates good antiperspirant efficacy, because peak 4 and 5 species are small size aluminum species. It is generally recognized that the small size of the aluminum species in antiperspirant solutions is responsible for its superior efficacy—small species are able to diffuse quickly and penetrate deep into the sweat duct. After penetrating, they obstruct the duct most likely by a combination of duct constriction and coagulation of matter in the duct (e.g., proteins).

The present inventors have further found that the SEC peak distribution of the ternary eutectic of urea, TMG, and $AlCl_3.6H_2O$ changes when the eutectic is heated at elevated temperature. In particular, without heating the Peak 5 species predominate together with some Peak 4 species. After a heating time of up to 1 hour, the Peak 5 species can be reduced and the Peak 4 species can be increased, so that the Peak 4 species predominate together with some Peak 5 species. With increasing heating times, the Peak 5 species disappear and Peak 3 species start to form. Therefore, for synthesizing the ternary eutectic of urea, TMG, and $AlCl_3.6H_2O$ it is preferred to minimize any heating at a temperature above the eutectic temperature in order to minimize the formation of larger size aluminum species of reduced antiperspirant efficacy.

The present inventors have found that antiperspirant compositions containing a metal salt, in particular an aluminum salt, and more particularly $AlCl_3.6H_2O$ as the active, can be present as a stabilized eutectic system in an anhydrous carrier at a higher pH, and so a much safer pH, than previous generation antiperspirant compositions containing $AlCl_3.6H_2O$ as the active. In particular, the present inventors have found an anhydrous eutectic carrier system that can stabilize an excess of the small aluminum species in those solutions of $AlCl_3.6H_2O$ at safe pH which can provide the desired mildness to skin and fabric. The antiperspirant composition can provide the combination of enhanced sweat protection from a known effective antiperspirant salt with the addition of improved mildness by raising the pH with a skin-compatible anhydrous carrier.

The present inventors have devised an anhydrous carrier system that can stabilize an excess of the small aluminum species in those solutions at a much milder pH. This provides an effective route to enhanced sweat protection because the technology is based on $AlCl_3.6H_2O$, and the present inventors have improved upon known negative effects of that active by providing a stable eutectic carrier which can be liquid at room temperature (e.g. below 30° C.) and can have a raised pH with a skin-compatible buffer which is part of the eutectic system, in particular the basic compound such as urea raising the pH.

It is known to add buffers, especially urea, to $AlCl_3.6H_2O$ solutions to increase the pH. However, it is not known to use a combination of a base such as a urea and at least one member chosen from a cation and zwitterion which together can form an anhydrous eutectic mixture which is a solvent for the antiperspirant active such as $AlCl_3.6H_2O$. The base such as urea can increase the pH of an antiperspirant active within the pH range of interest to the present antiperspirant compositions, and can be used to produce a eutectic composition of lower melting point which can act as a liquid solvent for the antiperspirant active, and optionally even the antiperspirant active forming a ternary eutectic with the carrier. It is also not known that such a combination of components in a ternary eutectic system can provide enhanced antiperspirant efficacy, high pH and stability of the antiperspirant composition.

In one embodiment, employed is, in an aqueous system, a zwitterion, specifically trimethylglycine, which aids synthesis of a eutectic system, stabilizes the product, and functions with urea, particularly when a 1:2 zwitterion to urea molar ratio is employed, as a complementary stabilizing system.

This permits the antiperspirant system, which may be a ternary eutectic mixture, to be synthesized in one step and in one pot. Such a simple synthesis can select between a multitude of reaction conditions that can be selected for specific outcomes, such as different pH, concentration, etc.

The preferred anhydrous antiperspirant system is based on a metal salt, a basic amide/amine, and at least one member chosen from a cation and zwitterion, preferably a proton-accepting zwitterionic methylamine, the latter typically being trimethylglycine, which is a permanent zwitterion, and which is not generally used in an antiperspirant preparation.

The preferred antiperspirant active can provide a number of technical benefits and advantages over known antiperspirant actives and systems.

In particular, the antiperspirant active may provide enhanced efficacy, so that extended protection can be achieved by stabilizing smaller aluminum species, which are known to be more effective antiperspirants. The antiperspirant active may provide reduced irritation and fabric damage by raising the pH of the aqueous solution. Such reduced irritation may be achieved by using an anhydrous skin-compatible buffering system, e.g. urea-trimethylglycine, for the active aluminum compound which forms a low melting point eutectic system. Furthermore, yellow staining can be reduced. Still further, reduced visibility of residue on skin and fabric can be achieved by stabilizing the active in an anhydrous carrier acting as a solvent rather than dispersing an opaque powder in a given formulation or by using an opaque formula base, for example a roll-on formulation.

The liquid anhydrous antiperspirant composition comprises a carrier that is a eutectic mixture of at least one basic compound selected from a basic amide and a basic amine and at least one member chosen from a cation and zwitterion.

Optionally, the at least one antiperspirant active, the at least one basic compound and the at least one member chosen from a cation and zwitterion form a ternary eutectic mixture.

Optionally, the at least one basic compound is a hydrogen bond donor and/or is selected from at least one of urea, dimethyl urea, arginine, lysine, acetamide, and guanidine. Optionally, the at least one member chosen from a cation and zwitterion is a proton-accepting zwitterionic stabilizing ligand. The at least one proton-accepting zwitterionic stabilizing ligand may comprise at least one methylamine, or may be selected from at least one of trimethylglycine, trimethylglycine hydrochloride, trimethylamine N-oxide (TMAO), carnitine, sarcosine, opine, taurine, and choline.

In a preferred embodiment, the at least one basic compound is urea and the at least one member chosen from a cation and zwitterion is trimethylglycine. The urea and trimethylglycine may be in a molar ratio of 9:1 to 1.5:1, optionally 5:1 to 3:1, optionally about 4:1.

In a preferred embodiment, the at least one basic compound is urea and the at least one member chosen from a cation and zwitterion is trimethylglycine, and the urea and trimethylglycine form a ternary eutectic mixture with the antiperspirant active.

Optionally, the antiperspirant active is present in an amount of 5 to 25 weight %. Optionally, the antiperspirant active comprises an aluminum salt, typically $AlCl_3.6H_2O$.

In a particularly preferred embodiment, the ternary eutectic mixture comprises $AlCl_3.6H_2O$ as the antiperspirant active, urea and trimethylglycine. Optionally, the ternary eutectic mixture comprises 5 to 25 wt % $AlCl_3.6H_2O$, 35 to 75 wt % urea, and 15 to 50 wt % trimethylglycine.

The antiperspirant composition typically has a pH of 2.5 to 6, optionally 3 to 5.

The anhydrous antiperspirant composition preferably comprises at most 2 wt % water.

The anhydrous carrier may be present in an amount that is more than any other single material in the composition. In certain embodiments, the carrier is at least 50 weight % of the composition. In other embodiments, the carrier is at least 55, 60, 65, 70, 75, 80, 85, or 90 weight % of the composition.

The combination of the at least one basic compound, which may be a hydrogen bond donor, and the at least one member chosen from a cation and zwitterion can form a deep eutectic solvent. A deep eutectic solvent is a mixture that forms a eutectic with a melting point lower than either of the individual components.

When urea is used to neutralize aluminum chloride, and trimethylglycine provides a stabilizing effect as a ligand, a liquid state antiperspirant composition is obtained that is mainly composed of the smaller aluminum species, which can be demonstrated by standard Size Exclusion Chromatograph (SEC). The SEC spectrum of this liquid state antiperspirant composition is dominated by "peak 4 or peak 5", which are the smaller aluminum species that are known to have very good antiperspirant efficacy.

In certain variations of the carrier comprising the trimethylglycine and urea embodiment, a portion of the urea can be replaced by other buffers or hydrogen bond donors. In one embodiment, 20-50 molar % of the urea can be replaced.

Antiperspirant actives include, but are not limited to, aluminum chloride, aluminum chlorohydrate, aluminum sesquichlorohydrate, aluminum-zirconium hydroxychlorides, complexes or adducts of the above-mentioned active ingredients with glycol, such as propylene glycol (for example, "Rehydrol"™ II antiperspirant from SummitReheis), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients, listed in the Food and Drug Administration's Monograph on Antiperspirant Drug Products for overall-the-counter human use (Oct. 10, 1973) can be used. Specific examples of commercialized aluminum-zirconium salts include AZP-908 and Z-576 from SummitReheis (Huguenot, N.Y.).

In other embodiments, the antiperspirant active is an aluminum salt and/or an aluminum-zirconium salt, such as those described above, that are further stabilized by betaine and a calcium salt. More information about betaine and calcium salt stabilized antiperspirant salts can be found in U.S. Patent Application Publication No. 2006/0204463 to Tang et al.

In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al.

In other embodiments, the type of salt of interest, an aluminum zirconium tetrasalt or octasalt free of glycine are used wherein aluminum zirconium salt is stabilized by betaine and has a metal to chloride ratio of about 0.9:1 to about 1.3:1 (and in other embodiments of about 0.9:1 to about 1.2:1 or about 0.9:1 to about 1.1:1). For the tetrasalt, the Al/Zr atomic ratio can be about 3.2:1 to about 4.1:1.0 and the betaine:zirconium mole ratio can be about 0.2:1 to about 3.0:1 (or in other embodiments of about 0.4:1 to about 1.5:1). Another salt that can be used is an aluminum chloride salt buffered by betaine, wherein the salt has a metal to chloride ratio of 0.9:1 to 1.3:1 (and in other embodiments of about 0.9:1 to about 1.2:1 or about 0.9:1 to about 1.1:1). For the octasalt the Al/Zr atomic ratio is about 6.2:1 to about 10.0:1 and the betaine:Zr mole ratio is about 0.2:1 to about 3.0:1 (or in other embodiments of about 0.4:1 to about 1.5:1). In one embodiment, in the case of a salt that contains zirconium, the betaine is incorporated during the synthesis of the salt so as to maximize the stabilizing effect this ingredient has (especially on the zirconium species). Alternatively, it can be post added to a glycine-free salt along with additional active phase ingredients to form a betaine stabilized active.

Examples of commercially available glycine-free low M:Cl ratio tetrasalts and octasalts include, but are not limited to, REZAL™ AZP 955 CPG and REZAL™ AZP 885 respectively (both from SummitReheis Chemical Company, Huguenot, N.Y.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

Additionally, the antiperspirant active can be a calcium salt stabilized antiperspirant active. Examples of calcium salt stabilized antiperspirant actives can be found in U.S. Patent Application Publication No. 2006/0204463.

In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active. Antiperspirant actives can include, but are not limited to, the following: astringent salt of aluminum, astringent salt of zirconium, aluminum bromohydrate, aluminum chlorohydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorhydrate. In another embodiment, the antiperspirant active is aluminum zirconium tetrachlorhydrex propylene glycol.

The amount of antiperspirant active can be any of the regulatory allowed amounts for each type of antiperspirant active. In certain embodiments, the amount is up to 25 weight % for an over the counter composition. In certain embodiments, the amount is 5 to 25 weight % of the composition. In other embodiments, the amount is at least 5, 10, or 15 up to 20 weight % of the composition.

Aluminum chloride refers to the hydrate forms. In one embodiment, the hydrate form comprises $AlCl_3 \cdot 6H_2O$. In one embodiment, the amount of aluminum chloride is up to 20 weight %. In other embodiments, the amount is up to 18, 17, 16, 15, 14, 13, 12, 11, 10, 9, 8, 7, 6, or 5 weight %.

Examples of deodorant actives include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyl-trimethylammomium bromide, cetyl pyridinium chloride, farnesol (3,7,11-trimethyl-2,6,10-dodecatrien-1-ol), bactericides, and/or bacteriostats. In certain embodiments, the amount of deodorant actives is 1 to 20 weight % of the composition.

A stabilizing agent can optionally be included in the composition. The stabilizing agent is any material that is present in an amount such that the composition is liquid below 100° C. The amount of stabilizing agent varies by the stabilizing capability of each stabilizing agent. In certain embodiments, the amount of stabilizing agent is 1 to 20 weight % of the composition. In other embodiments, the amount of stabilizing agent is at least 1, 2, 3, 4, 5, 6, 7, 8, 9, or 10 up to 20 weight % of the composition. In other embodiments, the amount is less than 20, 15, 10, 9, 8, 7, 6, 5, 4, 3, or 2 down to 1 weight % of the composition. Examples of stabilizing agents include, but are not limited to, PPG-14 butyl ether, chloride salts, sodium chloride (NaCl), potassium chloride, ammonium chloride, bromides, nitrates, organic acids, glycerin, alcohol, ethanol, and isopropanol.

In certain embodiments, the anhydrous liquid antiperspirant composition can be extremely viscous, and its skin-feel can be described as a mixture of greasy, sticky, and tacky. To improve the skin feel of the composition, skin-feel additives can be added. In one embodiment, the amount of skin-feel additives is 1 to 8 weight % of the composition. In other embodiments, the amount is at least 1, 2, 3, 4, or 5 up to 8 weight %. In other embodiments, the amount is less than 8, 7, 6, 5, 4, 3, or 2 down to 1 weight %. In certain embodiments, the amount of skin-feel additives is up to 10 weight % to allow for more delivery of the antiperspirant active.

The optional skin-feel additives that can be used include, but are not limited to, water, isopropanol, ethanol, cocamidopropyl betaine, cyclomethicone (such as DC345), PEG-12 dimethicone copolyol (DC5329), steareth-2/steareth-20, polyoxyethylene homopolymer (POLYOX™ WSR-N 750 from Dow Chemical), palm kernel oil, mineral oil, and silicone polyether wax (Silwax from Siltech).

Water: It is one of the easiest additives to combine with the anhydrous liquid antiperspirant composition, and even in small amounts it can improve viscosity. Because aluminum hydrolysis becomes an issue with increasing availability of water, the amount of added water in the examples below has been capped at 2 weight %. Although there is an improvement in the "spreadability" of anhydrous liquid antiperspirant composition when 2 weight % water is added, its tendency to bead increases and it forms large pools on the skin surface. This effect can be unappealing. The benefit is that the formula remains clear.

Isopropanol (70%): Because it is 30% water, only 6.7 weight % or less is combined with anhydrous liquid antiperspirant composition to keep additional water at 2 weight % or below. The alcohol will disperse in anhydrous liquid antiperspirant composition with vigorous shaking and remain dispersed for a limited time due to the emulsifying effect of water in the system. The dispersion will break after about an hour, and the alcohol will layer on top of the anhydrous liquid antiperspirant composition. A 6.7 weight % formulation is less viscous than the original anhydrous liquid antiperspirant composition and forms a white, opaque, lotion-like product. It is of a low enough viscosity to be applied via pump spray. When the minimum is applied (0.06-0.08 g/60-80 cm$^2$), it is easily spread across the skin and feels like petroleum jelly but less viscous. Beading is greatly reduced and is almost imperceptible. A satin sheen is left on the skin. Comments on the formulation describe an initial greasiness that fades with further spreading. The dispersion can be stabilized with 0.1-2 weight % cocamidopropyl betaine.

Isopropanol Alcohol (100%): Because there is no water, this can be added in whatever amount desired, however, total additives are typically capped at 10 weight % to maintain an anhydrous liquid antiperspirant composition potency of 90 weight % or greater. Addition of this has a noticeable effect on viscosity but not as much as 70% isopropanol. A 10 weight % formulation will form a rough dispersion (large droplets of isopropanol in anhydrous liquid antiperspirant composition), but will still spread nicely on the skin, and it is easily dispensed with a pump spray. The dispersion breaks in less than an hour (sometimes in minutes), and the product needs to be mixed between applications. Formulations with 100% isopropanol "dry" more quickly than those with 70%, and a thinner film is often achieved.

Ethanol (100%): It is similar in action to 100% isopropanol, but it is slightly more soluble in the anhydrous liquid antiperspirant composition. Also, most formulations with ethanol remain clear. Anhydrous liquid antiperspirant composition formulations with greater than 15 weight % ethanol have a viscosity and skin-feel close to that of current roll on products, but have an anhydrous liquid antiperspirant composition potency less than 85 weight %.

Cocamidopropyl betaine (CAPB): To retain the benefits of isopropanol-based formulations, an emulsifier can be added to stabilize the dispersion. Cocamidopropyl betaine comes as a 30% solution in water, which limits its total use in an anhydrous liquid antiperspirant composition formulation to no more than 3 weight %. This is not a problem considering effective amounts range from 0.1-2 weight % depending on the amount of isopropanol or other additives. Foaming can occur if the level is too high. Dispersions stabilized with cocamidopropyl betaine are typically semi-opaque white and lotion-like. Cocamidopropyl betaine improves the initial skin-feel of a formulation causing it to feel smoother and les sticky or tacky.

DC345 cyclomethicone from Dow Corning: It is hard to formulate with anhydrous liquid antiperspirant composition alone because the two tend to separate, and it causes the anhydrous liquid antiperspirant composition to bead even faster than normal. In amounts less than 0.5 weight %, DC345 can reduce tackiness in isopropanol-cocamidopropyl betaine systems without noticeable beading.

DC5329 (PEG-12 Dimethicone Copolyol): It is a silicone-based emulsifier that forms multilamellar vesicles (hydrophilic inside—hydrophobic between bilayers). It stabilizes oil-in-water and silicon-in-water formulations. Its recommended level of use is about 4 weight %. In certain embodiments, it can be used in anhydrous liquid antiperspirant compositions at 0.5-2 weight % where it will stabilize but also thicken formulations. 0.5 weight % in an isopropanol formulation will give the product more body but still spread nicely and improve skin adhesion.

Steareth-2/Steareth-20: These two ethoxylated fatty acids can be combined to stabilize an oil-in-water dispersion. They increase viscosity and waxiness in anhydrous liquid antiperspirant composition systems. Both are solids at room temp and must be melted together prior to addition, and the anhydrous liquid antiperspirant composition must be warm when formulating. The resulting formulation is opaque white and resembles a thick lotion.

Polyox™ WSR-N 750: This is a water soluble resin based on a linear poly(oxyethylene) homopolymer. It will dramatically increase slip and reduce drag during product application. It should be mixed with water before formulation with anhydrous liquid antiperspirant composition. Formulations are based on 0.5 weight % linear poly(oxyethylene) homopolymer (relative to anhydrous liquid antiperspirant composition) that are mixed with as little water as necessary to form a gel. The gel is added to the solid anhydrous liquid antiperspirant composition components and then baked. The gel plasticizes in the molten anhydrous liquid antiperspirant composition. The hardened gel is removed, and the anhydrous liquid antiperspirant composition with linear poly(oxyethylene) homopolymer is compared to normal anhydrous liquid antiperspirant composition. The viscosity is reduced, and skin adhesion is better. It is theorized that the water used to gel the linear poly(oxyethylene) homopolymer migrates into the anhydrous liquid antiperspirant composition, which causes the reduction in viscosity, and that only a (0.05 weight % or less w/w in anhydrous liquid antiperspirant composition) of the linear poly(oxyethylene) homopolymer actually makes it into the formulation.

The anhydrous liquid antiperspirant composition represents a new form of antiperspirant composition. Prior forms included sticks, soft solids, gels, aerosols, and water-based roll-ons. In these prior forms, antiperspirant actives are suspended and undissolved in the compositions. This prevents the formation of transparent compositions. Also, this leads to having white residue when applied to skin, which is undesirable to consumers. The anhydrous liquid antiperspirant provides a transparent product with no white residue (compatible to placebo). Also, there is long shelf life, for example up to 10 years can be expected.

The composition can optionally contain emollients in any desired amount to achieve a desired emollient effect. Emollients are known in the art and are used to impart a soothing effect on the skin. Non-volatile emollients are preferable. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material is phenyl trimethicone. Non-limiting examples of emollients can be found in U.S. Pat. No. 6,007,799. Examples include, but are not limited to, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate, Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide.

The composition can contain a fragrance. Any know fragrance can be used in any desired amount. In one embodiment, the amount of fragrance is 0.01 to 10 weight %.

Antioxidants may be added to the composition, preferably to act as ingredient protectants and for maintenance of long-term stability of the composition. Examples of antioxidants include, but are not limited to butylated hydroxytoluene, pentaerythrityl tetra-di-t-butyl hydroxyhydrocinnamate (Tinogard™ TT from Ciba).

Any of the anhydrous liquid antiperspirant compositions can be applied to axillary areas to reduce sweat and/or odor. The compositions can be applied by hand or via their packaging.

SPECIFIC EMBODIMENTS

The invention is further described in the following examples. The examples are merely illustrative and do not in any way limit the scope of the invention as described and claimed.

Example 1

A variety of urea/trimethylglycine (TMG) mixtures was prepared employing from 0 to 100 wt % urea and from 100 to 0 wt % TMG, and mixtures therebetween. Differential Scanning calorimetry (DSC) was used to characterize melting point of the resultant compositions as a function of TMG content. The results are shown in FIG. 1.

The results indicated that when the molar ratio of urea:TMG was within in the range of 9:1 to 1.5:1, a mixture was formed which had a melting point lower than either of the constituent compounds. The melting point reached a minimum temperature of about 90° C. when the molar ratio of urea:TMG was 4:1, in other words with 20 mol % TMG and 80 mol % urea.

When the urea/TMG mixture was cooled to room temperature, it crystallized over a period of 1-14 days.

An aluminum salt as an antiperspirant active was added to the eutectic mixture of urea/trimethylglycine (TMG). It was found that the eutectic mixture acted as an anhydrous solvent for the aluminum salt which dissolved in the eutectic mixture. The aluminum salt tested was $AlCl_3 \cdot 6H_2O$.

Furthermore, it was found that the addition of $AlCl_3 \cdot 6H_2O$ in amounts up to 25 wt % based on the total weight of the composition was capable of decreasing the melting point of the eutectic mixture to still further, to a range of 60-80° C. Therefore the dissolved aluminum salt was dissolved in the eutectic mixture of the anhydrous solvent to form a ternary eutectic mixture, with even lower melting point than the solvent itself.

In the presence of $AlCl_3 \cdot 6H_2O$, the mixtures were stable at temperatures below room temperature for an indefinite period of time.

Thus, the mixtures of urea/TMG both with and without $AlCl_3 \cdot 6H_2O$ are eutectic mixtures formed via a eutectic reaction.

Example 2

Four mixtures containing a molar ratio of urea:TMG of 2:1 and 18 wt %, based on the total weight of the composition, of $AlCl_3 \cdot 6H_2O$ were heated at 120° C. in sealed Teflon reaction vessels. The respective mixtures were heated for 1 hour, 2 hours, 3 hours, or 6 hours. After quenching the vessel in cool water, an aliquot of each eutectic was diluted to contain 1 wt % Al and immediately analyzed via SEC. The results are shown in FIG. 2.

Figure 2:
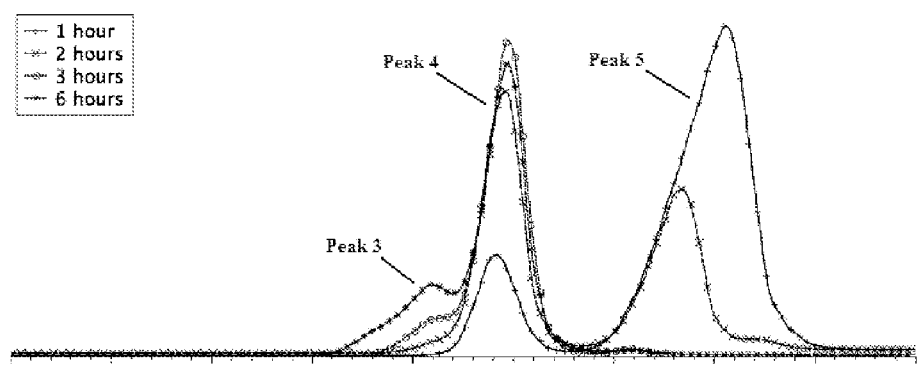
FIG. 2 is an SEC peak distribution of a ternary eutectic antiperspirant composition comprising a eutectic carrier and an antiperspirant active produced in accordance with an embodiment after heating for various time periods.

The SEC analysis shown in FIG. 2 clearly indicates a direct relationship between heating time and the Al species distribution. After heating for 1 hour, SEC peak 5 dominates the chromatogram. Heating times longer than 3 hours result in the complete elimination of Peak 5 and the predominance of Peak 4.

Similar results to those shown in FIG. 2 were obtained when the mixtures were heated in an open reaction vessel. It was noted that a clear liquid forms after about 20 minutes. The formation of the clear liquid was accompanied by vigorous bubbling which continued until the reaction was quenched. Based on the normal reactivity of urea, it is believed by the present inventors that urea degradation allows for the slow generation of hydroxide in the reaction mixture according to the following equation.

$$CO(NH_2)_2 + 3H_2O \rightarrow 2OH^- + 2NH_4^+ + CO_{2(g)} \qquad (1)$$

The water in equation (1) would be supplied from the coordination sphere of $AlCl_3 \cdot 6H_2O$. This conclusion is supported by the finding that fully anhydrous mixtures of urea, TMG, and anhydrous $AlCl_3$ do not evolve any gaseous products and exhibit only SEC peak 5.

The compositions were also subjected to $^{27}Al$ NMR analysis. The results are shown in FIG. 3.

Figure 3:
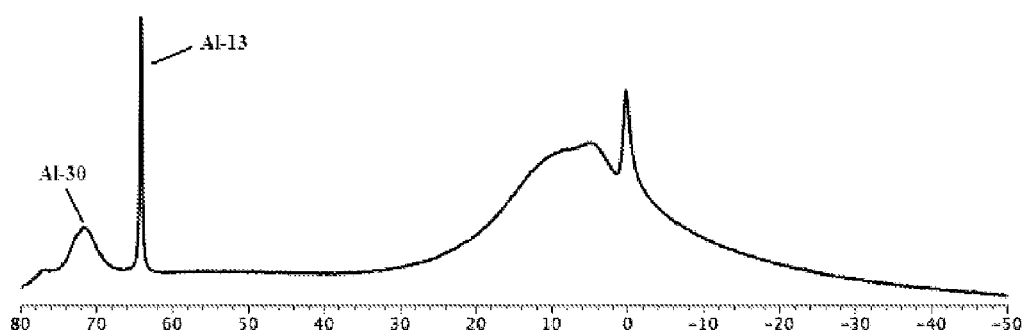
FIG. 3 shows a $^{27}$Al NMR spectrum of a ternary eutectic antiperspirant composition comprising a eutectic carrier and an antiperspirant active produced in accordance with an embodiment.

The $^{27}$Al NMR spectrum of the mixture heated for 2 hours showed five clearly identifiable chemical shift regions at about 0 ppm, 5 ppm, 10 ppm, 64 ppm, and 71 ppm, which shift regions corresponding respectively to Al monomers, Al dimers, $Al_{13\text{-}mer\ and\ 30\text{-}mer}$, $Al_{13\text{-}mer}$, and $Al_{30\text{-}mer}$ species, as shown in FIG. 3.

Urea does not appear to be coordinated to Al, as indicated by the absence of any resonance peaks with chemical shift values <0 ppm.

What is claimed is:

1. A method of producing an anhydrous antiperspirant composition, the method comprising the steps of:
 a) providing a mixture of at least one antiperspirant active including a metal salt, and an anhydrous carrier for the at least one antiperspirant active in which the at least one antiperspirant active is dissolved, the carrier comprising a eutectic mixture of at least one basic compound and at least one member chosen from a cation and zwitterion; and
 b) heating the mixture to form a stabilized eutectic system of the at least one antiperspirant active and the anhydrous carrier and
 wherein the at least one basic compound is urea and the at least one member chosen from a cation and zwitterion is trimethylglycine.

2. The method of claim 1, wherein the mixture comprises at most 2 wt % water.

3. The method of claim 1, wherein in step (b) the mixture is heated to melt the carrier and dissolve the at least one antiperspirant active therein.

4. The method of claim 3, wherein in step (b) the mixture is heated at a temperature below the melting temperature of each of the at least one basic compound and the at least one member chosen from a cation and zwitterion.

5. The method of claim 3, wherein in step (b) the mixture is heated at a temperature of at least 100° C. for a period of greater than 0 to less than 3 hours.

6. The method of claim 5, wherein in step (b) the mixture is heated at a temperature of at 100° C. to 150° C. for a period of 30 minutes to less than 3 hours.

7. The method of claim 1, wherein the stabilized eutectic system is a liquid at a temperature of up to 100° C.

8. The method of claim 1, wherein the at least one antiperspirant active, the at least one basic compound and the at least one member chosen from a cation and zwitterion form a ternary eutectic system.

9. The method of claim 1, wherein the urea and trimethylglycine are in a molar ratio of 9:1 to 1.5:1.

10. The method of claim 9, wherein the urea and trimethylglycine are in a molar ratio of about 4:1.

11. The method of claim 1, wherein the antiperspirant active is present in an amount of 5 to 25 weight %.

12. The method of claim 1, wherein the antiperspirant active comprises an aluminum salt.

13. The method of claim 12, wherein the antiperspirant active comprises $AlCl_3.6H_2O$.

14. The method of claim 8, wherein the ternary eutectic mixture comprises $AlCl_3.6H_2O$ as the antiperspirant active, urea and trimethylglycine.

15. The method of claim 14, wherein the ternary eutectic mixture comprises 5 to 25 wt % $AlCl_3.6H_2O$, 35 to 75 wt % urea, and 15 to 50 wt % trimethylglycine.

16. The method of claim 1, wherein the anhydrous antiperspirant composition has a pH of 2.5 to 6.

\* \* \* \* \*